United States Patent
Greenhalgh

(10) Patent No.: US 6,814,754 B2
(45) Date of Patent: Nov. 9, 2004

(54) WOVEN TUBULAR GRAFT WITH REGIONS OF VARYING FLEXIBILITY

(75) Inventor: E. Skott Greenhalgh, Wyndmoor, PA (US)

(73) Assignee: Secant Medical, LLC, Perkasie, PA (US)

(*) Notice: Subject to any disclaimer, the term of this patent is extended or adjusted under 35 U.S.C. 154(b) by 0 days.

(21) Appl. No.: 10/003,901

(22) Filed: Oct. 25, 2001

(65) Prior Publication Data

US 2002/0058992 A1 May 16, 2002

Related U.S. Application Data

(60) Provisional application No. 60/244,240, filed on Oct. 30, 2000.

(51) Int. Cl.[7] .................................................. A61F 2/06
(52) U.S. Cl. .................................................... 623/1.51
(58) Field of Search .................. 600/36; 623/FOR 100, 623/1.3, 1.31, 1.35, 1.51, 1.52, 23.71, 1.32, 1.33, 1.36, 1.53

(56) References Cited

U.S. PATENT DOCUMENTS

| | | | |
|---|---|---|---|
| 967,585 A | | 8/1910 | Teufel |
| 2,117,974 A | | 5/1938 | Moore |
| 3,304,557 A | | 2/1967 | Polansky |
| 5,653,746 A | * | 8/1997 | Schmitt ...................... 128/898 |
| 5,800,514 A | | 9/1998 | Nuñez et al. |

FOREIGN PATENT DOCUMENTS

WO    WO 99/40875    *   8/1999    .............  A61F/2/06

* cited by examiner

Primary Examiner—David H. Willse
(74) Attorney, Agent, or Firm—Synnestvedt & Lechner LLP

(57) ABSTRACT

A woven tube having a warp direction oriented lengthwise to the tube and a fill direction oriented circumferentially of the tube is disclosed. The tube is woven from a plurality of elastic warp yarns arranged parallel to the warp direction and a plurality of elastic fill yarns arranged parallel to the fill direction. The tube has one or more discrete regions of relatively greater flexibility formed in either the warp or fill directions at locations along the tube. The flexibility is oriented in the warp direction or the fill direction by weaving either the warp or fill yarns, respectively, under relatively less tension.

21 Claims, 5 Drawing Sheets

WOVEN TUBULAR GRAFT WITH REGIONS OF VARYING FLEXIBILITY

RELATED APPLICATION

This application is based on and claims priority of U.S. Provisional Application No. 60/244,240, filed Oct. 30, 2000.

FIELD OF THE INVENTION

This invention relates to woven tubular grafts having selected regions of varying flexibility and particularly to woven bifurcated tubes for use as endoluminal grafts in the treatment of vascular aneurysms.

BACKGROUND OF THE INVENTION

A vascular aneurysm is a pathologic dilation of a segment of a blood vessel which constitutes a weakened portion of the vessel. FIG. 1 shows an example of a fusiform aneurysm 10, such as can occur in the abdominal aorta 12. The entire circumference of the aorta 12 is dilated and weakened. The majority of these aortic aneurysms are located in the distal abdominal aorta between the renal arteries 14 and the bifurcation point 16 where the abdominal aorta splits into the common iliac arteries 18.

An aneurysm in any vascular vessel is a cause of concern, and aortic aneurysms in particular constitute a serious condition, as an acute rupture of the aneurysm is fatal unless an emergency operation is performed. However, even when such operations are performed in time, the mortality rate is still greater than 50%.

Modern methods of treatment for aneurysms focus on preventing rupture by providing a stent graft which is positioned within the artery at the aneurysm. As seen in FIG. 1 by way of example, a stent graft 20 comprises a bifurcated fabric tube 22. Bifurcated fabric tubes are formed of a plurality of interlaced yarns wherein a single tube branches into two or more tubes at a bifurcation point. The term "yarn" as used herein is a generic term for a continuous strand or strands of fibers, filaments or material in a form suitable for knitting, weaving, braiding or otherwise intertwining or interlacing to form a fabric. Various forms of yarn include monofilaments, filaments twisted together, filaments laid together without twist, as well as other configurations.

Tube 22 may be woven, knitted or braided and has one end 24 which is attached to the inner surface of the artery upstream of the aneurysm 10. The opposite end 26 of the bifurcated tube is split at a septum 28 into two branch tubes 26a and 26b. The branch tubes are attached to the inside surfaces of the iliac arteries 18 below the aneurysm 10. The stent graft 20 is substantially impermeable to blood and replaces the abdominal aorta in the region of the aneurysm 10, relieving the pressure on the weakened arterial wall and avoiding a potentially fatal rupture.

For endoluminal stent grafts, which are implanted in the artery through the use of a catheter, woven tubes are preferred because the graft should have as little bulk as possible so that it may be readily collapsible to fit within the lumen of the catheter. As noted above, the graft must also be substantially impermeable in the region of the aneurysm so as to isolate and relieve the pressure on it. Woven structures inherently have relatively minimal bulk when compared to knitted or braided structures having the same dimensions and can readily form a substantially impermeable membrane with low porosity. Because bifurcated grafts, with their multiple tubes, tend to be bulkier than grafts comprising a single tube, the woven structure which minimizes the bulk is especially advantageous.

The advantages of small bulk and low porosity for woven endoluminal grafts are obtained at a significant disadvantage in that the woven tube is generally unable to stretch elastically in either the radial or longitudinal directions. The lack of flexibility is inherent in woven fabrics due to the limited relative motion afforded to the yarns, which are substantially locked in place due to the nature of the weave and the requirement of impermeability. The lack of flexibility results in the disadvantages described below for the example of the woven bifurcated tube used as a graft for the repair of an aortic aneurysm. It is understood that the examples provided below apply to other than bifurcated tubes in the repair of other types of aneurysms as well.

Blood vessels are seldom round in cross-section; they tend to be oval, egg-shaped or have irregular shapes due to calcified deposits formed on the inner walls. The woven bifurcated tube must sealingly join the vessel at both its ends, but the lack of radial flexibility inhibits the ability of the tube to adapt to the non-round cross section of the vessel. As shown in FIG. 2, this may result in folds 30 in either or both the vessel 12 and the tube 22 where they are joined at upstream end. The folds can result in leakage of blood past the graft at its upstream end and into the aneurysm, placing pressure on the aneurysm and possibly causing it to burst.

Blood vessels are seldom straight; they tend to curve in complex ways. This is readily apparent in bifurcated vessels such as the abdominal aorta 12 which in which branches 26a and 26b curve away into the iliac arteries 18 supplying blood to the lower extremities. The lack of longitudinal flexibility inhibits the woven graft from readily bending to follow the curvature of the iliac arteries as they branch away from the aorta. As seen in FIG. 3, the branch 26a of the woven tube 22 may tend to buckle and bunch up on the inside part of the curve, causing folds 32 which can occlude the lumen of the graft, restricting blood flow. The part of the branch 26a on the outside of the curve does not stretch to accommodate the longer path of the artery wall and tends to tug on the artery, perhaps causing a kink 34 in its wall.

Blood vessels tend to vary in diameter from person to person depending on the physical characteristics of the individual. Due to their inherent lack of radial flexibility, woven tubes of one particular diameter cannot readily adapt to the range of artery sizes among different people. As shown in FIG. 4, if the tube 22 is too small in diameter, it may cause folds 36 in the artery 12, reducing the blood flow and causing leaks past the joint. If the tube is too large, it may tend to form an inward fold 38 and leak, as seen in FIG. 5. Therefore, many sizes of grafts must be available so that the appropriate size may be matched to a particular artery size so that a good seal can be obtained between graft and artery.

Blood vessels tend to enlarge in diameter with the age of the patient. The woven tube 22 generally does not have sufficient radial flexibility to accommodate the expansion of the vessel 12 and may result in a separation 40 of a portion of the graft from the wall of the vessel as seen in FIG. 6. This may allow leakage into the aneurysm, and in extreme cases the upstream portion of the tube may fold into the lumen, inhibiting the flow of blood through the vessel.

Woven tubes with little radial or axial elasticity tend to be stiff. This stiffness directly affects the force required to move the stent graft through the lumen of a catheter for positioning the graft within the artery at the aneurysm. The catheter is seldom straight as it must follow the bends and twists of the vessel through which it snakes, and the stiffer the graft is, the more force is required to move it through a twisting catheter lumen.

There is clearly a need for an endoluminal graft which has minimal bulk so that it will fit within the lumen of a catheter, is substantially impermeable and strong enough to withstand repeated hydraulic pressure cycles caused by hundreds of thousands of heart beats and yet possesses the radial and longitudinal flexibility, allowing it to move with minimal force through a curving catheter and to sealingly accommodate arteries of various shapes, sizes and curvatures without folding or kinking in order to form and maintain a fluid-tight seal between the graft and the artery in the treatment of aneurysms.

SUMMARY AND OBJECTS OF THE INVENTION

The invention concerns a graft compatible with living tissue, the graft comprising an elongated tube woven from a plurality of warp yarns oriented in a warp direction substantially lengthwise along the tube and a plurality of fill yarns oriented in a fill direction substantially circumferentially around the tube. The warp and the fill yarns are elastic, and the tube comprises a region of relatively greater flexibility oriented in one of the warp and the fill directions.

The region of relatively greater flexibility is formable in the warp direction by weaving the warp yarns comprising the region under relatively less tension than the tension at which the warp yarns comprising the remainder of the tube are woven. The region of relatively greater flexibility is formable in the fill direction by weaving the fill yarns comprising the region under relatively less tension than the tension at which the fill yarns comprising the remainder of the tube are woven.

It is advantageous to have a region of relatively greater flexibility oriented in the fill direction and located at one end of the tube, the region of relatively greater flexibility being formed by weaving the plurality of the fill yarns comprising the region under relatively less tension than the tension at which the fill yarns comprising the remainder of the tube are woven. Such a tube may also comprise a second region of relatively greater flexibility oriented again in the fill direction and located at an opposite end of the tube, the second region of relatively greater flexibility also being formed by weaving the plurality of the fill yarns comprising the second region under relatively less tension than the tension at which the fill yarns comprising the portion of the tube between the first and second regions are woven.

It is also possible to have a third region of relatively greater flexibility oriented in the warp direction and located between the first and second regions of relatively greater flexibility. The third region of relatively greater flexibility is formed by weaving the plurality of warp yarns comprising the third region under relatively less tension than the tension at which the warp yarns comprising the first and second regions of relatively greater flexibility are woven.

The region of relatively greater flexibility may also be formed in the warp direction by including in the region relatively fewer of the warp yarns per unit area than the number of the warp yarns per unit area comprising the remainder of the tube. Similarly, the region of relatively greater flexibility may also be formed in the fill direction by including in the region relatively fewer of the fill yarns per unit area than the number of the fill yarns per unit area comprising the remainder of the tube.

The invention also includes a method of making a graft comprising an elongated tube compatible with living tissue and having a region of relatively greater flexibility. The method according to the invention comprises the steps of:

(1) weaving a plurality of elastic warp yarns oriented in a warp direction substantially lengthwise along the tube at a first predetermined tension with a plurality of elastic fill yarns oriented in a fill direction substantially circumferentially around the tube at a second predetermined tension; and (2) weaving at least some of the yarns at a third predetermined tension relatively less than the first and the second tensions thereby forming the region of relatively greater flexibility, the flexibility being greater in the warp direction when the plurality of the warp yarns are woven at the third predetermined tension, the flexibility being greater in the fill direction when the fill yarns are woven at the third predetermined tension.

According to the method, a plurality of fill yarns may be woven at the third tension over a portion of the tube positioned at one end, thereby forming the region of relatively greater flexibility at the one end, the increased flexibility being in the fill direction.

Furthermore, the plurality of fill yarns may also be woven at the third tension over a second portion of the tube positioned at an opposite end thereof, thereby forming a second of the regions of relatively greater flexibility at the opposite end of the tube, the increased flexibility also being in the fill direction at the opposite end.

It is also advantageous to weave the plurality of warp yarns at the third tension over a third portion of the tube positioned between the ends, thereby forming a third region of relatively greater flexibility, the increased flexibility being in the warp direction over the portion between the ends.

It is an object of the invention to provide a woven graft having regions of differing flexibility in the warp and fill directions.

It is an object of the invention to provide a woven graft having relatively greater radial flexibility at its ends for accommodating an irregularly shaped vessel.

It is another object of the invention to provide a woven graft having relatively greater radial flexibility at its ends for accommodating a vessel whose diameter changes over time.

It is still another object of the invention to provide a woven graft having greater flexibility in the warp direction allowing the graft to stretch lengthwise and follow a curved path within a vessel.

It is yet another object of the invention to provide a woven graft having relatively greater flexibility without increasing the bulk of the graft.

It is again another object of the invention to provide a woven graft which will pass through a catheter relatively easily.

These and other objects and advantages of the invention will become apparent upon consideration of the following drawings and detailed description of the preferred embodiments.

DETAILED DESCRIPTION OF THE PREFERRED EMBODIMENTS

The disadvantages of the woven tube enumerated above can be avoided while maintaining its advantages of strength, impermeability and minimal bulk by selectively controlling the elastic properties of the tube during the weaving process to provide a tube having relatively greater flexibility over certain regions and relatively less flexibility in other regions.

Figure 7:
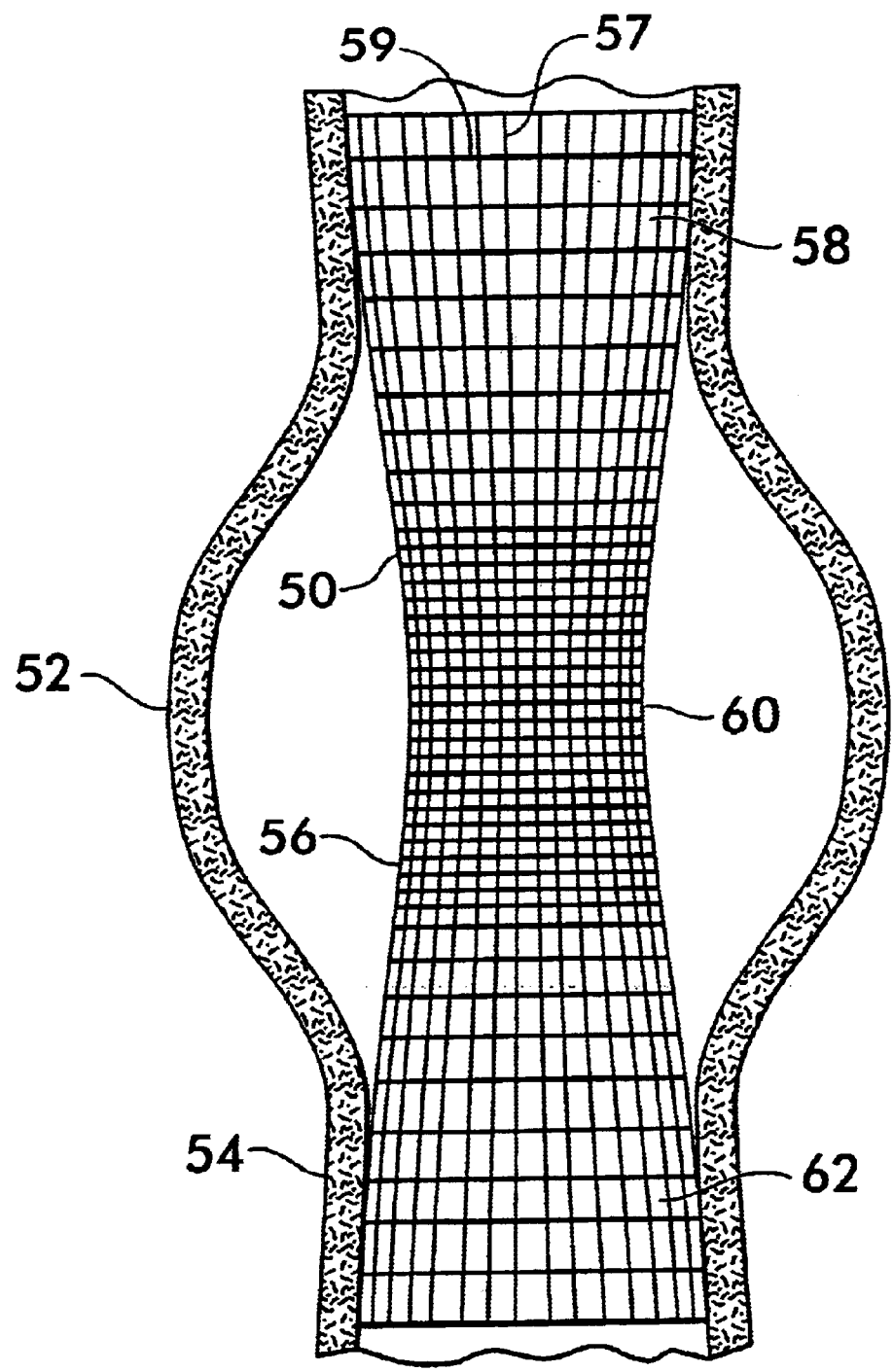
FIG. 7 is a graft comprising a woven tube according to the invention.

FIG. 7 shows an endoluminal stent graft 50 used to treat a fusiform aneurysm 52 in an artery 54. Stent graft 50 comprises a tube 56 woven from a plurality of warp yarns 57 and fill yarns 59 and having three regions, 58, 60 and 62, of differing flexibility. Regions 58 and 62 form the upstream and downstream ends, respectively, of the tube 56, where the tube attaches circumferentially around the artery 54 and must form a seal which will prevent leaks into the aneurysm 52. As noted above, arteries are not usually round, may have calcified occlusions, are different in size from one another and may tend to expand in diameter with age. In order to ensure a proper seal between the tube 56 and the artery 54, it is advantageous to provide increased radial flexibility to the tube in regions 58 and 62. This allows these regions to stretch and match the particular size and shape of the artery and accommodate any surface irregularities caused by deposits or occlusions. The increased radial flexibility also enhances the compliance of the tube, ensuring that the seal between tube and artery is maintained over time as the artery increases in diameter.

Radial flexibility of the regions 58 and 62 is controlled by using elastic fill yarns 59 in the fill direction circumferentially around the tube and varying the tension and density at which these fill yarns are woven. When relatively greater radial flexibility is desired over the regions, the fill yarns are woven under relatively less tension and/or at relatively lower density (picks per length of tube) than other regions of the tube. Because they are woven under less tension, the elastic yarns are locked into the fabric substantially unstretched and are subsequently able to stretch elastically in the fill direction when required to allow radial expansion of the tube to match the diameter and shape of the artery. The lower density of the fill yarns also increases the radial flexibility as there are generally fewer yarns per unit area which must be stretched, allowing the regions 58 and 62 to be expanded by relatively lower loads than if a higher density of yarns were used. A side benefit of the lower weave density at the end regions 58 and 62 is that it may provide interstices of a size which encourage the ingrowth of endothelial cells which line the artery, thereby effecting a natural seal between graft and vessel.

It is not desirable that the tube 56 have significant radial flexibility in the region 60 adjacent to aneurysm 52. This region must maintain its diameter under the hydraulic pressure of the blood as it is pumped through the artery so that it relieves the pressure on the aneurysm 52. Significant radial flexibility in this region would defeat the purpose of the graft as it would allow the tube 56 to expand and place pressure on the artery at the aneurysm.

The radially stiff region 60 is formed by weaving the elastic fill yarns comprising the tube under relatively higher tension than the fill yarns in regions 58 and 62. Preferably, the tension is above the elastic limit but below the ultimate tensile strength of the fill yarns in region 60. The yarns, stretched by the tension force during weaving and locked in the fabric in the stretched state, are not capable of further significant stretching elastically when radial forces are applied to the interior of the tube, as occurs, for example, due to the hydraulic pressure during heartbeats. The density of the fill yarns may also be increased to provide further radial stiffness to the tube in region 60. With more yarns per unit length, it requires greater force to radially expand the tube, yielding relatively greater stiffness in the fill direction for the region 60. Greater yarn density also has the added benefit of reducing the porosity and preventing leakage of blood from the stent graft at the aneurysm.

The tension of the fill yarns 59 is controlled by the loom's shuttle trigger tension, which can be set to a relatively low value when region 58 is being woven, resulting in substantially unstretched fill yarns and a tube having relatively greater radial flexibility and compliance over region 58. The shuttle trigger tension may be increased as region 60 is being woven to insert substantially stretched yarns in the fill direction, yielding a relatively stiff tube radially over region 60. As region 62 is woven, the shuttle trigger tension is again reduced, inserting substantially unstretched fill yarns under low tension and producing a region of the tube having relatively greater radial flexibility and compliance.

The density of the fill yarns may be controlled by a pick wheel as is well understood in the art.

The elastic yarns used to weave tube 56 are preferably highly textured yarns of polyester. Polytetrafluoroethylene, polypropylene or other biocompatible materials are also feasible. The textured nature of the yarns provides the required elastic properties. Alternatively, the elastic property of the yarns may be obtained by using inherently elastic materials, such as silicone, polyurethane or rubber to form the yarns. Crimped yarns may also be employed to provide fill yarns wherein the tension may be varied to change the radial stiffness of the tube.

A practical example of a stent graft 50 may comprise a tube 12 inches in length, 1.2 inches in diameter, having fill yarns of textured polyester of 40 denier initially woven at a shuttle trigger tension of 100 grams and a fill density of 60 picks per inch to form region 58. The shuttle trigger tension is then increased to 140 grams and the fill density of the fill yarns is increased to 68 picks per inch to weave region 60, being relatively stiffer in the fill direction. Region 62 is then woven at the same parameters as region 58, although the parameters need not be the same.

Figure 8:
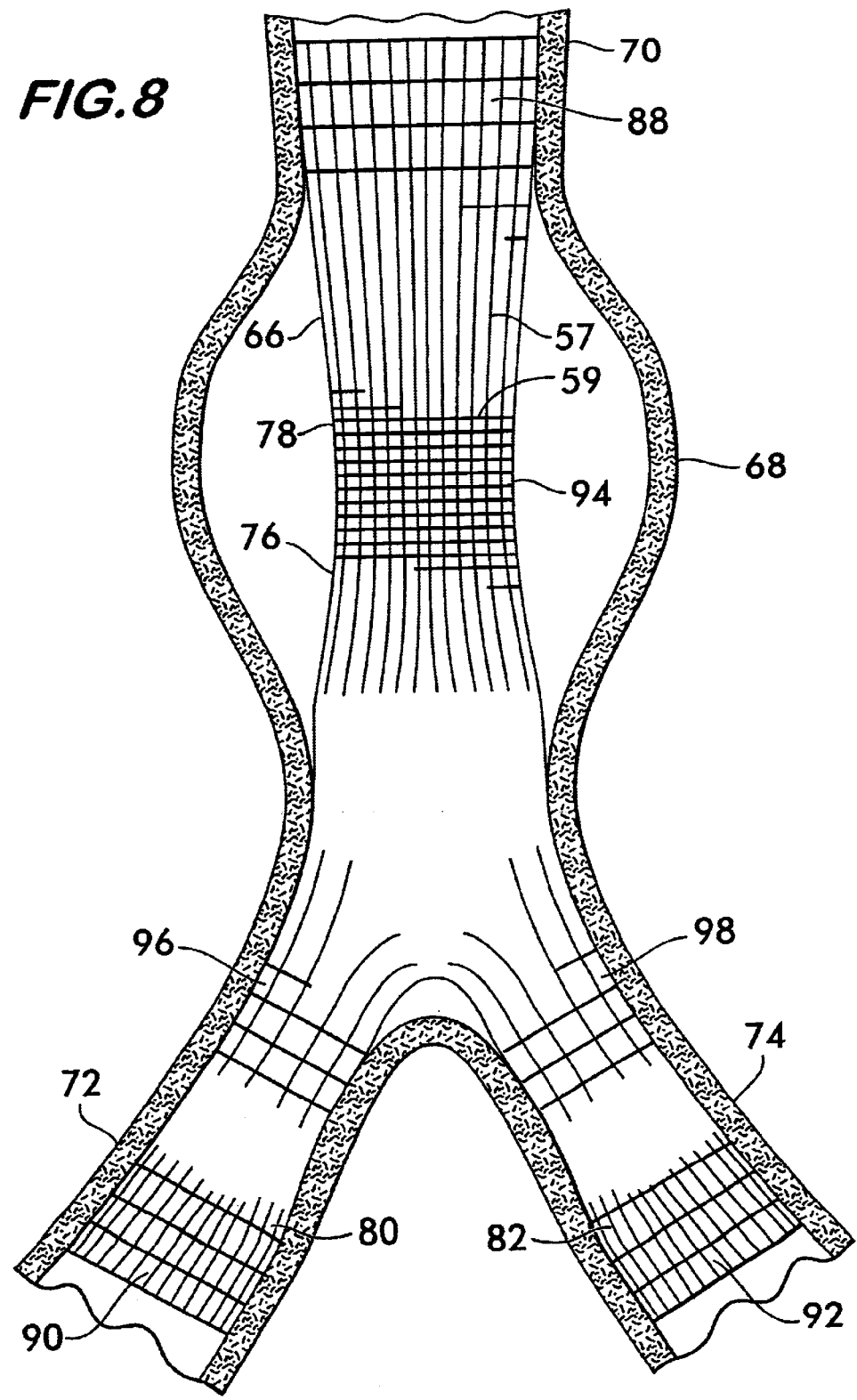
FIG. 8 is a graft comprising a bifurcated woven tube according to the invention.

FIG. 8 shows a stent graft 66 used to treat a fusiform aneurysm 68 in an aortic artery 70 near the iliac arteries 72 and 74. Stent graft 66 comprises a bifurcated tube 76 having a main tube 78 and two branch tubes 80 and 82. Both the main and branch tubes are woven from a plurality of warp yarns 57 and fill yarns 59, the warp yarns being oriented in a warp direction oriented lengthwise along the main and branch tubes, the fill yarns being oriented in a fill direction circumferentially around the tubes. Bifurcated tube 76 provides an example of a stent graft which will benefit from controlling the flexibility of the tube in both the fill and warp directions.

As described above for the tube 56, it is advantageous to provide relatively greater flexibility oriented in the fill direction (circumferentially) in regions of tube 76 such as 88, 90 and 92 which are areas where the tube requires greater radial compliance and flexibility to effect a seal to the artery.

As noted above, relatively low radial flexibility is desired for the region 94 adjacent to the aneurysm. The radial flexibility characteristics for the bifurcated tube 76 are controlled in the same way as described above for the conventional tube 56, i.e., by controlling the tension under which the fill yarns are woven when forming the various regions of the tube.

Figure 1:
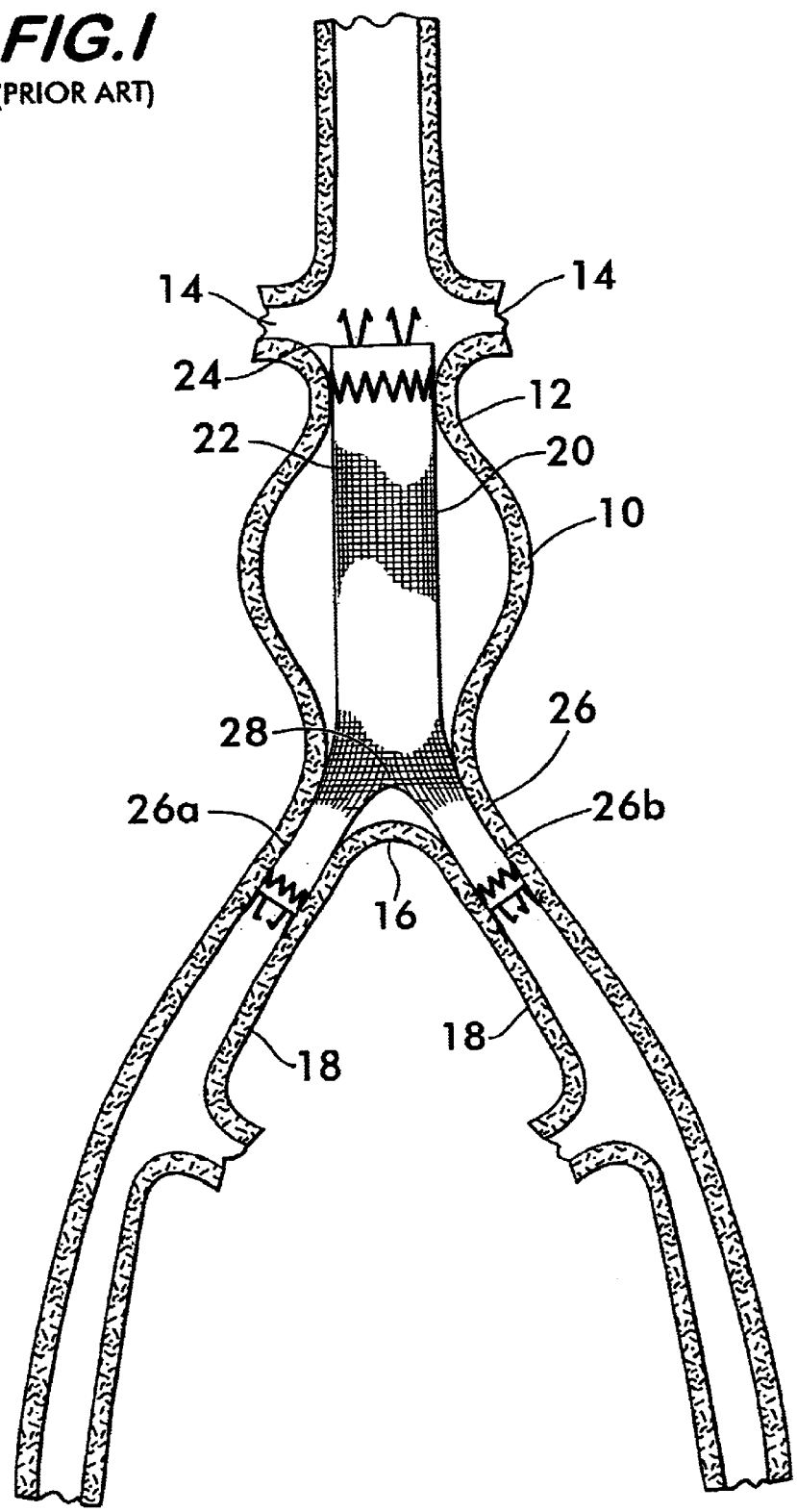
FIG. 1 is a partial sectional view of a graft according to the prior art.
Figure 2:
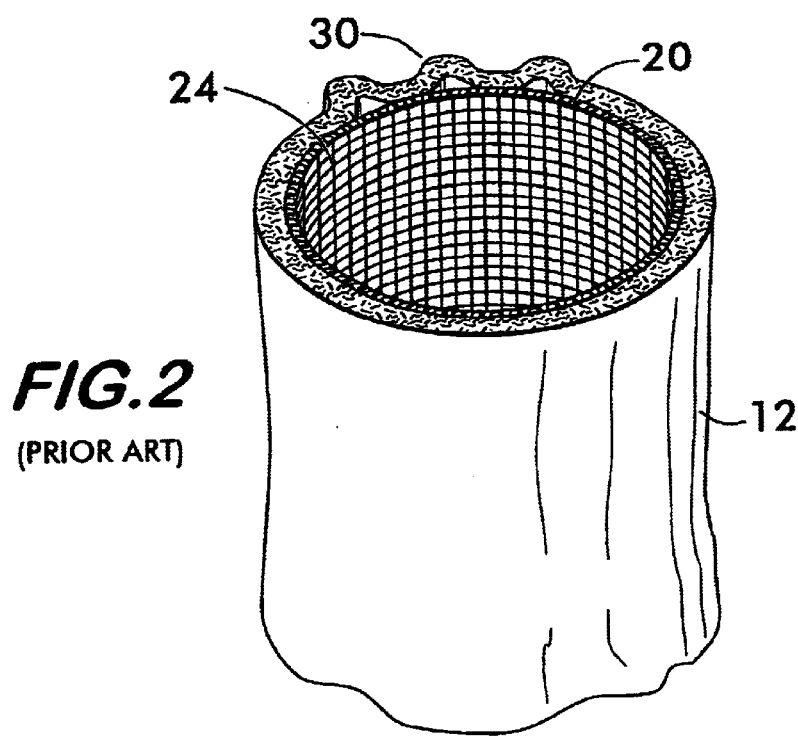
FIG. 2 is a partial perspective view of a graft according to the prior art.
Figure 3:
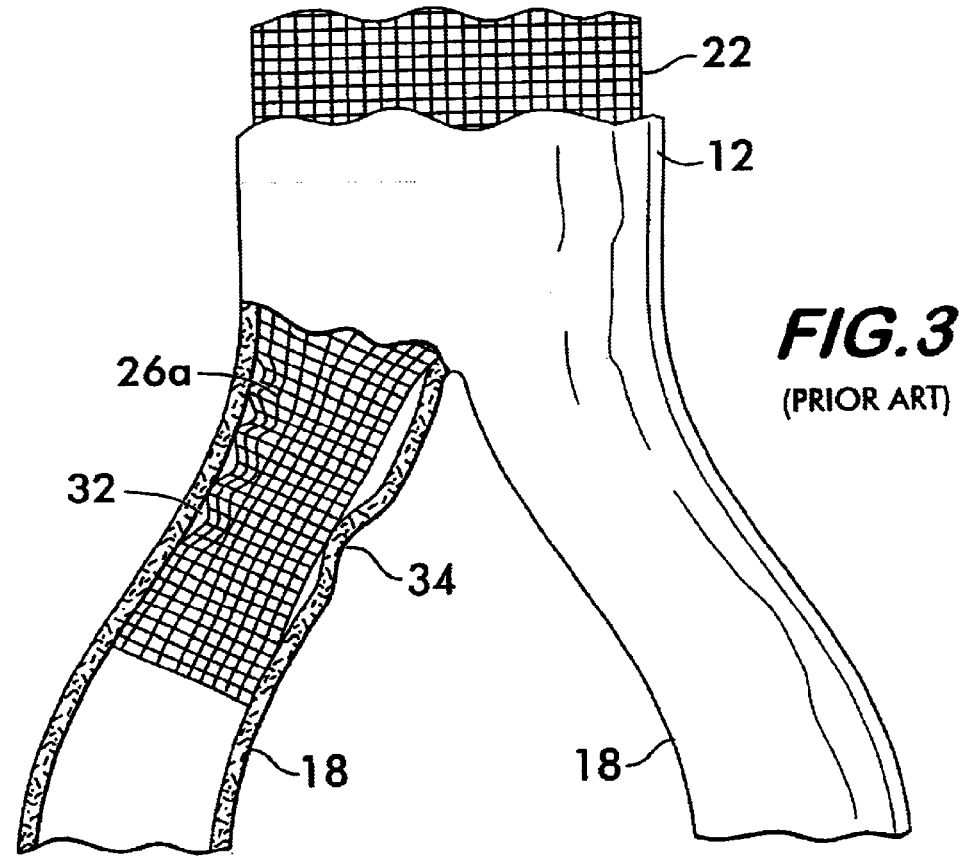
FIG. 3 is a partial sectional view of a graft according to the prior art.
Figure 4:
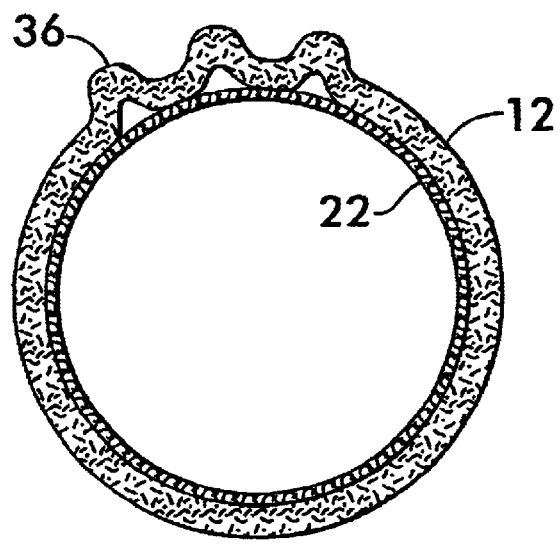
FIG. 4 is a cross-sectional view of a graft according to the prior art.
Figure 5:
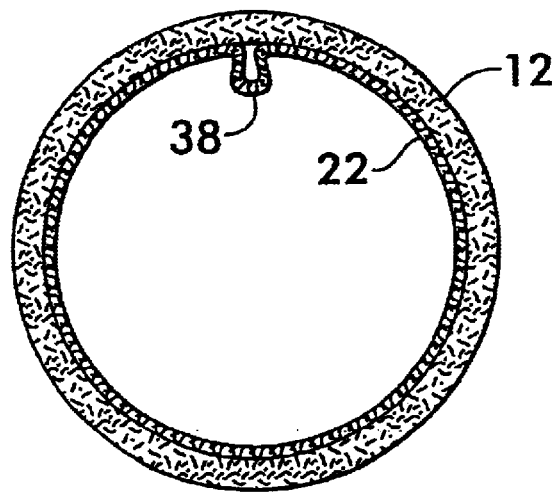
FIG. 5 is a cross-sectional view of a graft according to the prior art.
Figure 6:
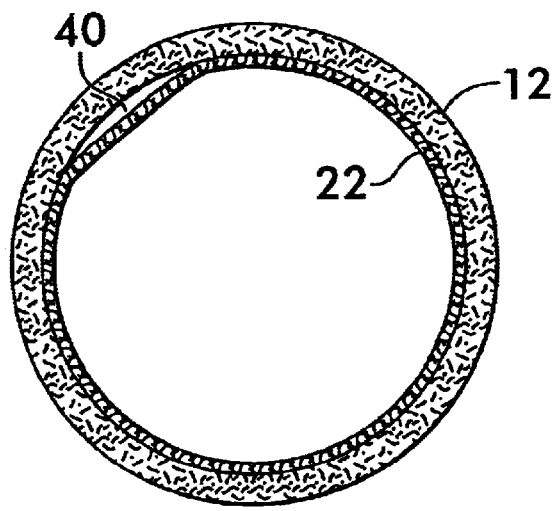
FIG. 6 is a cross-sectional view of a graft according to the prior art.

However, for regions 96 and 98 on branch tubes 80 and 82, it is also advantageous to have relatively greater flexibility in the warp direction lengthwise along the branch tubes. Greater flexibility in the warp direction will permit the branch tubes 80 and 82 to follow the curvature of the iliac arteries 72 and 74 without folding on the inside of the curve or kinking on the outside of the curve as seen in FIG. 3.

The relative flexibility of the branch tubes 80 and 82 in the warp direction over regions 96 and 98 is controlled by using elastic warp yarns in the warp direction and weaving the warp yarns under relatively greater or lesser tension. If relatively greater flexibility in the warp direction is desired, the warp yarns are woven under relatively less tension than other regions of the tube 76. The warp yarns woven under the lower tension are substantially unstretched when they are woven into the fabric and will, therefore, be able to stretch elastically under load, allowing the tube to stretch lengthwise and accommodate the curvature of the artery. Conversely, if relatively less flexibility is desired in the warp direction, the warp yarns are stretched under relatively greater tension (preferably in excess of the elastic limit) as they are woven into the fabric. The stretched yarns are locked into the fabric by the fill yarns and provide relatively little lengthwise flexibility since they are already stretched above their elastic limit and have little or no elasticity left.

As with the fill yarns, the warp yarns are preferably highly textured yarns comprised of polyester, polytetrafluoroethylene, polypropylene or other biocompatible materials.

Further control of the longitudinal flexibility may be provided by weaving the tube 76 with the warp yarns closer or farther apart, thereby controlling the warp yarn density (the number of yarns per unit length). Denser weaves are necessarily woven under relatively higher yarn tension which tends to pre-stretch the yarn, leaving little capacity for the yarn to stretch further once woven into the tube. This results in a tube with relatively less flexibility in the warp direction but achieves relatively low fabric porosity due to the relatively higher yarn density. In contrast, less dense weaves are woven under relatively less tension, and the warp yarns are not pre-stretched to the same degree and, when interwoven to form the tube, consequently allow it to stretch with relatively greater longitudinal flexibility. Such tubes have relatively higher porosity, however, and are, therefore, more permeable. Control of the warp yarn density may be effected by varying the separation of the tines of the comb through which the warp yarns pass on the loom.

A practical example of a bifurcated tube 76 useable as a stent graft may comprise a main tube 5 inches in length, 1.2 inches in diameter and branch tubes 6 inches in length and 0.7 inches in diameter, the tubes being formed of textured polyester yarns of 40 denier. Fill yarns 59 in regions 88, 90 and 92 near the ends of the tubes are woven at a shuttle trigger tension of 100 grams and a fill density of 60 picks per inch to provide relatively greater flexibility in the fill direction, allowing the tube to expand radially and accommodate and seal to the vessel 70. By contrast, the fill yarns in region 94, located adjacent to the aneurysm 68, are woven at an increased shuttle trigger tension of 140 grams, and the fill density may be increased to 68 picks per inch to provide relatively less flexibility in the fill direction over region 94.

Regions 88 and 94 are woven with warp yarns under a relatively high tension of 10 grams to provide relatively lower warp direction flexibility over these regions. However, the warp yarn tension and density is changed when branch tubes 80 and 82 are being woven. To provide relatively greater warp direction flexibility, thereby allowing the branch tubes to better follow the curve of the iliac arteries 72 and 74, the warp yarn tension is reduced to 7 grams and the warp yarn density is reduced from 140 to 130 ends per inch.

Fabric tubes with regions of varying flexibility in the warp and fill directions according to the invention will provide improved stent grafts for the repair of vascular aneurysms. Relatively greater flexibility in the fill direction will provide for a better seal between the graft and the artery, lessening the likelihood of leakage or obstruction of the artery and allow one size of graft to accommodate a wide range of different size and shape arteries. Relatively greater flexibility in the warp direction will allow the graft to conform to the curvature of the artery as it twists and bends without folding or causing kinking of the vessel. The overall increased flexibility is attained without significantly increasing the bulk of the graft thus allowing the graft to be more easily moved through a catheter for delivery to the site of the aneurysm.

What is claimed is:

1. A graft compatible with living tissue, said graft comprising an elongated tube woven from a plurality of warp yarns oriented in a warp direction substantially lengthwise along said tube and a plurality of fill yarns oriented in a fill direction substantially circumferentially around said tube, said warp and said fill yarns being elastic, at least some of said yarns being woven under relatively less tension over a portion of said tube than other of said yarns thereby forming a region of said tube substantially coincident with said portion and having relatively greater flexibility than the remainder of said tube.

2. A graft according to claim 1, wherein said yarns woven under relatively less tension comprise warp yarns, said region of relatively greater flexibility being oriented in said warp direction thereby allowing said tube to stretch lengthwise.

3. A graft according to claim 2, wherein said region of relatively greater flexibility is positioned over a portion of said tube between ends of said tube.

4. A graft according to claim 1, wherein said yarns woven under relatively less tension comprise fill yarns, said region of relatively greater flexibility being oriented in said fill direction thereby allowing said tube to stretch radially outwardly.

5. A graft according to claim 4, wherein said region of relatively greater flexibility is positioned over a portion of said tube at one end thereof.

6. A graft compatible with living tissue, said graft comprising an elongated tube woven from a plurality of warp yarns oriented in a warp direction substantially lengthwise along said tube and a plurality of fill yarns oriented in a fill direction substantially circumferentially around said tube, said warp and said fill yarns being elastic, said tube comprising a region of relatively greater flexibility oriented in one of said warp and said fill directions, said region of relatively greater flexibility being formable oriented in said warp direction by weaving said warp yarns comprising said region under relatively less tension than the tension at which said warp yarns comprising the remainder of said tube are woven, said region of relatively greater flexibility being formable oriented in said fill direction by weaving said fill yarns comprising said region under relatively less tension than the tension at which said fill yarns comprising the remainder of said tube are woven.

7. A graft according to claim 6, wherein said region of relatively greater flexibility is further formable in said warp direction by including in said region relatively fewer of said warp yarns per unit length than the number of said warp yarns per unit length comprising the remainder of said tube, said region of relatively greater flexibility being further formable in said fill direction by including in said region relatively fewer of said fill yarns per unit length than the number of said fill yarns per unit length comprising the remainder of said tube.

8. A graft according to claim 6, wherein said region of relatively greater flexibility is oriented in said fill direction and located at one end of said tube, said region of relatively greater flexibility being formed by weaving said plurality of said fill yarns comprising said region under relatively less tension than the tension at which said fill yarns comprising the remainder of said tube are woven.

9. A graft according to claim 8, further comprising a second region of relatively greater flexibility oriented in said fill direction and located at an opposite end of said tube, said second region of relatively greater flexibility being formed by weaving said plurality of said fill yarns comprising said second region under relatively less tension than the tension at which said fill yarns comprising a portion of said tube between said first named and said second regions are woven.

10. A graft according to claim 9, further comprising a third region of relatively greater flexibility oriented in said warp direction and located between said first named and said second regions of relatively greater flexibility, said third region of relatively greater flexibility being formed by weaving said plurality of said warp yarns comprising said third region under relatively less tension than the tension at which said warp yarns comprising said first named and said second regions of relatively greater flexibility are woven.

11. A graft according to claim 10, wherein said tube comprises a bifurcated tube.

12. A graft according to claim 6, wherein at least one of said plurality of said warp yarns and said fill yarns comprises yarns selected from among the group consisting of highly textured polyester, polypropylene and polytetrafluoroethylene yarns.

13. A graft according to claim 6, wherein at least one of said plurality of said warp yarns and said fill yarns comprises yarns selected from among the group consisting of silicone, polyurethane and rubber yarns.

14. A graft compatible with living tissue, said graft comprising an elongated bifurcated tube comprising a main tube connected with two branch tubes in fluid communication with said main tube, said bifurcated tube terminating in a first end positioned distally from said branch tubes, each of said branch tubes terminating in an end distally from said main tube, said bifurcated tube being woven from a plurality of warp yarns oriented in a warp direction substantially lengthwise along said main and said branch tubes and a plurality of fill yarns oriented in a fill direction substantially circumferentially around said main and said branch tubes, said warp and said fill yarns being elastic, said ends having relatively greater flexibility in said fill direction than said main and said branch tubes between said ends, said ends being formed by weaving said plurality of said fill yarns comprising said ends under relatively less tension than the tension at which said plurality of said fill yarns comprising said main and said branch tubes between said ends are woven.

15. A graft according to claim 14, wherein said main and said branch tubes between said ends have relatively greater flexibility in said warp direction than said ends, said main and said branch tubes between said ends being formed by weaving said plurality of said warp yarns comprising said main and said branch tubes under relatively less tension than the tension at which said plurality of said warp yarns comprising said ends are woven.

16. A graft compatible with living tissue, said graft comprising an elongated tube woven from a plurality of warp yarns oriented in a warp direction substantially lengthwise along said tube and a plurality of fill yarns oriented in a fill direction substantially circumferentially around said tube, said warp and said fill yarns being elastic, said tube comprising first and second regions of relatively greater flexibility positioned at opposite ends of said tube, said first and second regions of greater flexibility being oriented in said fill direction and being formed by including in said first and second regions relatively fewer of said fill yarns per unit length than the number of said fill yarns per unit length comprising the remainder of said tube.

17. A graft according to claim 16, further comprising a third region of relatively greater flexibility oriented in said warp direction and located between said first and said second regions of relatively greater flexibility, said third region of relatively greater flexibility being formed by including in said third region relatively fewer of said warp yarns per unit length than the number of said warp yarns per unit length comprising said first and said second regions of relatively greater flexibility.

18. A method of making a graft comprising an elongated tube compatible with living tissue and having a region of relatively greater flexibility, said method comprising the steps of:

weaving a plurality of elastic warp yarns oriented in a warp direction substantially lengthwise along said tube at a first predetermined tension with a plurality of elastic fill yarns oriented in a fill direction substantially circumferentially around said tube at a second predetermined tension; and weaving at least some of said yarns over a portion of said tube at a third predetermined tension relatively less than said first and said second tensions thereby forming over said portion said region of relatively greater flexibility, said flexibility being greater in said warp direction if said warp yarns are woven at said third predetermined tension over said portion, said flexibility being greater in said fill direction if said fill yarns are woven at said third predetermined tension over said portion.

19. A method according to claim 18, wherein said fill yarns are woven at said third tension over said portion of said tube, said portion being positioned at one end thereof, thereby forming said region of relatively greater flexibility at said one end, said increased flexibility being in said fill direction.

20. A method according to claim 19, wherein said fill yarns are woven at said third tension over a second portion of said tube positioned at an opposite end thereof, thereby forming a second region of relatively greater flexibility at said opposite end, said increased flexibility being in said fill direction at said opposite end.

21. A method according to claim 20, in said warp yarns are woven at said third tension over a third portion of said tube positioned between said ends, thereby forming a third region of relatively greater flexibility, said increased flexibility being in said warp direction over said third portion between said ends.

* * * * *